US007807467B2

(12) United States Patent
Lodrigueza

(10) Patent No.: US 7,807,467 B2
(45) Date of Patent: Oct. 5, 2010

(54) METHOD FOR PREDICTION OF HIGH FREQUENCY RECIPROCATING RIG WEAR SCAR DIAMETER FOR HYDROCARBON MIXTURES BASED ON MID-INFRARED SPECTROSCOPY

(75) Inventor: Enrico A. Lodrigueza, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 1006 days.

(21) Appl. No.: 11/581,859

(22) Filed: Oct. 17, 2006

(65) Prior Publication Data

US 2008/0090302 A1 Apr. 17, 2008

(51) Int. Cl.
*G01N 33/24* (2006.01)

(52) U.S. Cl. .......................... 436/29; 436/25; 436/139; 436/164

(58) Field of Classification Search .................. None
See application file for complete search history.

(56) References Cited

U.S. PATENT DOCUMENTS

| | | | | |
|---|---|---|---|---|
| 5,740,073 | A | 4/1998 | Bages et al. | 364/499 |
| 6,159,255 | A | 12/2000 | Perkins | 44/300 |
| 6,546,782 | B1 | 4/2003 | De La Cruz et al. | 73/7 |
| 6,589,302 | B1 | 7/2003 | De Rosa et al. | 44/418 |
| 2004/0010963 | A1 | 1/2004 | Cross et al. | 44/333 |

OTHER PUBLICATIONS

Fodor et al. "Estimation of Middle Distillate Fuel Properties by FT-IR", Appl. Spectr., 1999, v. 53, No. 10, pp. 1292-1298.*
Hutzler et al. "Estimating Chemical and Bulk Properties of middle Distillate Fuels from Near-Infrared Spectra", Interim Report TRLRF No. 348, 2000.*
Chalk "Progress Report for Fuels for Advanced CIDI Engines and Fuel Cells", Annual Progress Report, 2000.*
"Operating Manual for Turbine/Diesel Fuel Analyzer", Aug. 2004.*
Wissner Ethos Fuel Reformulator, published before 1997, http://www.ethosfreast.com/Lubricity_RealCostofLubrication.html.*
Overview of HFRR, PCS Instruments, http://www.pcs-instruments.com/hfrr/hfrr.shtml.*
HFRR ASTM D6079-99: "Standard Test Method for Evaluating Lubricity of Diesel Fuels by the High Frequency Reciprocating Rig (HFRR)", 2007 http://www.eng.wayne.edu/page.php?id=4971.*
Crockett et al. "Wear and electrical resistance on diesel lubricated surfaces undergoing reciprocating sliding", Tribology Lett., 2004, v. 16, No. 3, pp. 187-194.*
Hutzler et al., "Estimating Chemical and Bulk Properties of Middle Distillate Fuels from Near-Infrared Spectra," Southwest Research Institute Interim Report TFLRF No. 348, DTIC No. A D A 394209.
Fodor et al., "Estimation of Middle Distillate Fuel Properties by FT-IR and Chemometrics, Part 1. Calibrations and Validations," Southwest Research Institute, Interim Report TFLRF No. 321, Dec. 1997.

* cited by examiner

*Primary Examiner*—Yelena G Gakh

(57) ABSTRACT

A method is disclosed for predicting the High Frequency Reciprocating Rig (HFRR) wear scar diameter for a hydrocarbon mixture using an HFRR wear scar diameter prediction equation which predicts the HFRR wear scar diameter based on the mid-infrared spectroscopy test results for such hydrocarbon mixture. Such predicted HFRR wear scar diameter value can then be used to determine the necessity of adding a lubricity additive to a diesel material in order to produce a diesel product possessing adequate lubricity properties.

18 Claims, 2 Drawing Sheets

Property: HFRR

METHOD FOR PREDICTION OF HIGH FREQUENCY RECIPROCATING RIG WEAR SCAR DIAMETER FOR HYDROCARBON MIXTURES BASED ON MID-INFRARED SPECTROSCOPY

In one aspect, the invention relates to a method to predict the High Frequency Reciprocating Rig (HFRR) wear scar diameter for hydrocarbon mixtures. In another aspect, the invention relates to a method of producing a diesel product possessing adequate lubricity properties.

BACKGROUND OF THE INVENTION

The ASTM has set lubricity standards for diesel fuels sold in the United States of America. The applicable test method is ASTM D-6079 which measures the HFRR wear scar diameter for the subject fuel. Such HFRR wear scar diameter is an indirect measure of the fuels lubricity. The ASTM D-6079 test is not amenable to use in the field, such as at a tank farm or a products terminal, is expensive to run, and can take on average around seventy-five minutes to complete. Due to the difficulty, expense, and impracticality, of testing diesel products for lubricity in the field, many diesel suppliers add more lubricity enhancing additives to their diesel products than is necessary in order to ensure compliance with the diesel lubricity specifications. I have discovered a method to predict the HFRR wear scar diameter for a hydrocarbon mixture, such as a diesel product, using an interaction model equation to correlate mid-infrared spectroscopy properties of a hydrocarbon mixture to its HFRR wear scar diameter.

SUMMARY OF THE INVENTION

It is an object of the present invention to provide a method to predict the HFRR wear scar diameter for hydrocarbon mixtures.

It is yet another object of the present invention to provide a method to predict the HFRR wear scar diameter for hydrocarbon mixtures using an interaction model equation to correlate mid-infrared spectroscopy properties of a hydrocarbon mixture to its HFRR wear scar diameter.

It is still a further object of the present invention to provide an economical and efficient method to produce a diesel product possessing adequate lubricity properties.

In accordance with one embodiment of the present invention, a method has been discovered for predicting the HFRR wear scar diameter for a hydrocarbon mixture comprising the steps of:

(a) selecting control hydrocarbon mixtures having various measured HFRR wear scar diameters as measured using the test method ASTM D-6079;

(b) subjecting each of the control hydrocarbon mixtures to mid-infrared (MIR) spectroscopy testing to thereby produce control property results for each of the control hydrocarbon mixtures;

(c) selecting an interaction model equation comprising a plurality of terms which relates MIR spectroscopy property results to HFRR wear scar diameters;

(d) establishing an HFRR wear scar diameter prediction equation by: 1) determining a set of coefficients for the terms of the interaction model equation by applying regression techniques to the control property results and the measured HFRR wear scar diameters, and 2) testing the statistical significance of each of the coefficients and the corresponding terms, and 3) retaining from the interaction model equation only those of the coefficients and corresponding terms which are statistically significant, to thereby establish the HFRR wear scar diameter prediction equation;

(e) subjecting the hydrocarbon mixture to MIR spectroscopy testing to thereby produce MIR spectroscopy property results; and (f) predicting the HFRR wear scar diameter value for the hydrocarbon mixture using the MIR spectroscopy property results in the HFRR wear scar diameter prediction equation.

In accordance with another embodiment of the present invention, a method has been discovered for producing a diesel product comprising the steps of:

a) subjecting a diesel material to MIR spectroscopy testing to thereby produce MIR spectroscopy property results;

b) predicting the HFRR wear scar diameter value for the diesel material using the MIR spectroscopy property results and the HFRR wear scar diameter prediction equation of the above described embodiment;

c) comparing the HFRR wear scar diameter value to a target HFRR wear scar diameter value; and d) producing the diesel product by either:
1) adding a lubricity additive to the diesel material if the HFRR wear scar diameter value is greater than the target HFRR wear scar diameter value to thereby produce the diesel product; or
2) not adding a lubricity additive to the diesel material if the HFRR wear scar diameter value is less than the target HFRR wear scar diameter value, and utilizing the diesel material as the diesel product.

In accordance with another embodiment of the present invention, a method has been discovered for predicting the HFRR wear scar diameter value for a diesel material comprising the steps of:

a) subjecting a sample of a diesel material to MIR spectroscopy testing to thereby produce MIR spectroscopy property results;

b) predicting the HFRR wear scar diameter value for the diesel material using the MIR spectroscopy property results in the HFRR wear scar diameter prediction equation of the above described embodiment.

Other objects and advantages will become apparent from the detailed description and the appended claims.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION OF THE INVENTION

Figure 1:
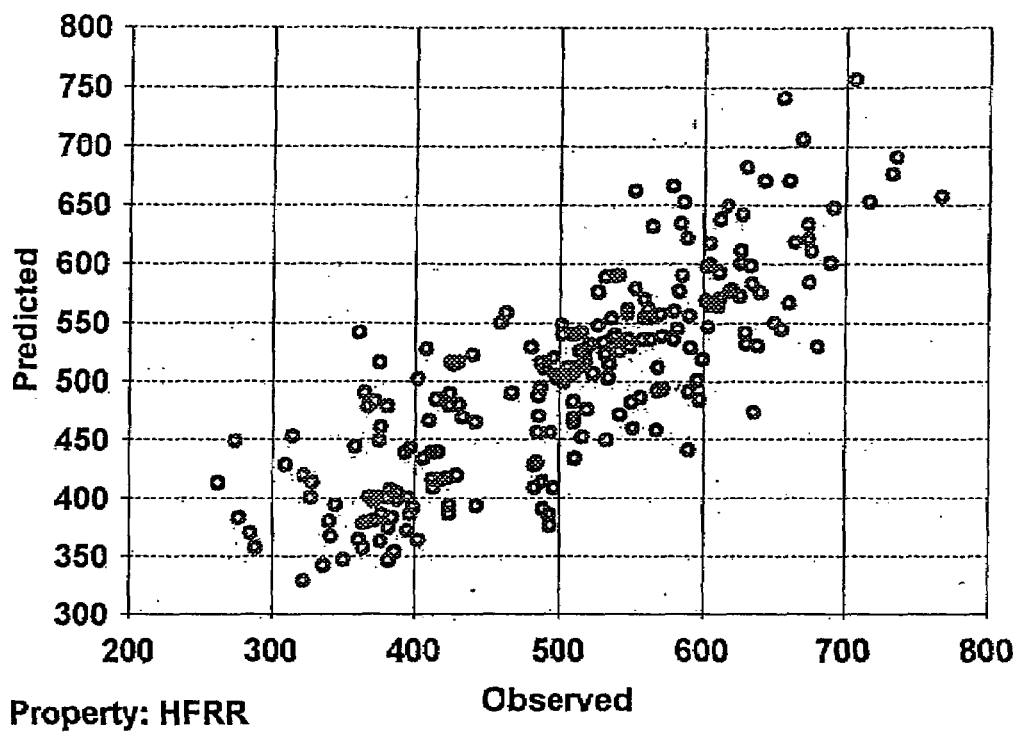
FIG. 1 depicts a plot of predicted vs. observed HFRR wear scar diameters based on the unadjusted interaction model equation.

Control hydrocarbon mixtures useful in the invention can be selected from any range of hydrocarbons for which HFRR wear scar diameter values are sought. More particularly, the control hydrocarbon mixtures are each diesel range materials. The control hydrocarbon mixtures comprise hydrocarbons preferably having from 9 to 23, more preferably from 11 to 22, and most preferably from 12 to 20 carbon atoms per molecule. Similarly, the hydrocarbon mixture of the present invention can be selected from any range of hydrocarbons for which HFRR wear scar diameters are sought. More particularly, the hydrocarbon mixture is a diesel range material. Preferably, the hydrocarbons of the hydrocarbon mixture have from 9 to 23, more preferably from 11 to 22, and most preferably from 12 to 20 carbon atoms per molecule.

Several different control hydrocarbon mixtures are selected and subjected to testing using the ASTM D-6079 test method to produce measured HFRR wear scar diameter values. Preferably, the number of different control hydrocarbon mixtures selected is about three times the number of terms of the hereinafter described interaction model equation. Each of the control hydrocarbon mixtures are then subjected to mid-infrared (MIR) spectroscopy testing to thereby produce control property results for each of the control hydrocarbon mixtures. The control property results correspond to the absorption value of particular chemical components or functional groups obtained from the MIR spectra. Any spectroscopy instrument capable of producing MIR spectroscopy results can be used in the present invention. Typical chemical components or functional groups useful in producing control property results can be selected from the following group:

methyl, methylene, alkyl nitrate, naphthalenes, aromatics, alkenes, poly nuclear aromatics, and biphenyls.

An interaction model equation is selected which comprises a plurality of terms and is useful for relating MIR spectroscopy property results to HFRR wear scar diameters. The interaction model equation preferably contains at least about 15 terms, more preferably at least about 20 terms, and most preferably at least about 28 terms. The interaction model equation is preferably based on multi-linear regression (MLR) analysis having the form:

$$P_x = M_0 + M_1 * F_1 + M_2 * F_2 + \ldots M_z * F_z$$

where $P_x$=value for property x; which corresponds to an HFRR wear scar diameter $F_z$=absorbance value from filter z; which correspond to the terms described above, and, regarding the regression, correspond to the control property results.

$M_z$=parameter estimate from filter z based on MLR analysis; which correspond to the coefficients for the terms, $M_0$=intercept of model.

An HFRR wear scar diameter prediction equation is then established by:

i) determining a set of coefficients for the terms of the interaction model equation by applying regression techniques to the control property results and the measured HFRR wear scar diameters, and ii) testing the statistical significance of each of the coefficients and the corresponding terms, and retaining from the interaction model equation only those of the coefficients and corresponding terms which are statistically significant, to thereby establish the HFRR wear scar diameter prediction equation.

Statistical significance for each of the coefficients resulting from the regression is determined, and the HFRR wear scar diameter prediction equation is established, by the following steps:

(I) determining the base Root MSE value and the base R-Square value for the interaction model equation based on the regression in step i) set out above;

(II) removing a term from the interaction model equation to form a test equation;

(III) determining a test set of coefficients for the terms of the test equation by applying regression techniques to the control property results and the measured HFRR wear scar diameters;

(IV) determining the test equation Root MSE value and the test equation R-Square value for the test equation based on the regression of Step (III);

(V) if 1) the test equation Root MSE value is less than the base Root MSE value, and 2) the test equation R-Square value is greater than or equal to the base R-Square value; then: use the test equation as the interaction model equation, use the test equation Root MSE value as the base Root MSE value, and use the test equation R-Square value as the base R-Square value;

(VI) repeating steps (II)-(V) until each of the plurality of terms of the interaction model equation has been once removed from the interaction model equation in step (II); and (VII) using the interaction model equation resulting from step (VI) as the HFRR wear scar diameter prediction equation.

The hydrocarbon mixture is then subjected to MIR spectroscopy testing to thereby produce MIR spectroscopy property results. Such MIR spectroscopy property results are then used in the HFRR wear scar diameter prediction equation to produce a predicted HFRR wear scar diameter value for the hydrocarbon mixture.

In another embodiment of the invention, the HFRR wear scar diameter prediction equation is used as a tool in the production of a diesel product which possesses adequate lubricity properties.

Diesel materials useful in producing a diesel product in accordance with this embodiment of the invention, and either at a refinery or at a product terminal, can be any diesel range material suitable for use in a diesel engine. Such diesel materials comprise hydrocarbons preferably having from 9 to 23, more preferably from 11 to 22, and most preferably from 12 to 20 carbon atoms per molecule.

The method of this embodiment includes the following steps:

a) A diesel material from above is subjected to MIR spectroscopy testing to produce MIR spectroscopy property results.

b) The HFRR wear scar diameter value for such diesel material is then predicted using the MIR spectroscopy property results in the HFRR wear scar diameter prediction equation described above.

c) The HFRR wear scar diameter value is compared to a target HFRR wear scar diameter value for the particular diesel product to be produced. Such target HFRR wear scar diameter value is preferably the HFRR wear scar diameter specification value set out in the most current revision of ASTM D-975 currently entitled "Standard Specification for Diesel Fuel Oils". The target HFRR wear scar diameter value is more preferably about 520 µm, and even more preferably about 480 µm.

d) The diesel product is then produced by either 1) adding a lubricity additive to the diesel material if the HFRR wear scar diameter value is greater than the target HFRR wear scar diameter value to thereby produce the diesel product; or 2) not adding a lubricity additive to the diesel material if the HFRR wear scar diameter value is less than the target HFRR wear scar diameter value, and utilizing the diesel material as the diesel product.

Steps a), b) and c) set out above can be performed at a laboratory or a retail site.

In accordance with another embodiment of the invention, steps a) and b) from the above embodiment can be used to predict the HFRR wear scar diameter value for a diesel material, without necessarily using such value to produce a diesel product in accordance with the method of the previous embodiment.

Any additive suitable for improving the lubricity of a diesel product can be used as the lubricity additive. Lubricity additives can contain either aliphatic ester derivatives, amides or different types of carboxylic acids.

The following example is presented to further illustrate the invention and is not to be construed as unduly limiting its scope.

EXAMPLE

This example illustrates the development of a HFRR wear scar diameter prediction equation using an interaction model equation in accordance with the invention.

The following steps were followed to develop the HFRR wear scar diameter prediction equation for this Example.

1) A total of 214 control diesel mixtures were tested using the test method ASTM D-6079 to determine their respective HFRR wear scar diameter values. The control diesel mixtures were also each subjected to MIR spectroscopy testing using a PetroSpec Turbine/Diesel analyzer obtained from PAC Petroleum Analyzer Company L.P. producing absorption values (control property results) for each.

The analyzer used had fourteen filters (each filter produces an absorbance value for the feed tested) related to the following functional groups:

Filter Group
F1: methyl
F2: methylene
F3: Alkyl nitrate/Naphthalenes
F4: Filter 3 baseline correction
F5: Aromatic
F6: Alkene
F7: Alkene
F8: Naphthalenes
F9: Aromatic 3 adjacent hydrogens/Naphthalenes
F10: Aromatic 4 adjacent hydrogens
F11: Biphenyl
F12: Aromatic symmetrical tri-substituted
F13: Aromatic 5 adjacent hydrogens
F14: Polynuclear Aromatics The interaction model equation used in this example also included fourteen additional control property result terms which are the squares of the absorbance values and are represented as F1SQ to F14SQ. These non-linear terms are also used in the interaction model equation.

2) The HFRR wear scar diameter values (Px in the model) and the control property results (Mz terms in the model); (collectively the "control data") were inputted into an interaction model equation having 29 terms loaded on a PetroSpec Turbine/Diesel Analyzer (the terms being the Intercept, F1-F14, and F1SQ-F14SQ).

3) Multi-linear regression was then performed on the control data using the interaction model equation resulting in a set of coefficients for the terms of the unadjusted interaction model equation and resulting in a base Root MSE value and a base R-Square value. The base Root MSE value, and base R-Square value for the unadjusted interaction model equation were 67.12 and 0.6656, respectively. The plot of predicted vs. observed (measured) HFRR wear scar diameters for the 214 control diesel mixtures based on the unadjusted interaction model equation is shown in FIG. 1.

4) One of the terms, and corresponding coefficient, was then removed from the interaction model equation to form a test equation.

5) A new set of coefficients for the remaining terms were determined for the test equation by applying regression techniques to the control property results entered and the measured HFRR wear scar diameters.

6) The test equation Root MSE and test equation R-Square values were determined for the test equation and compared to the base Root MSE and base R-Square values.

If:

i) the test equation Root MSE value was less than the base Root MSE value, and ii) the test equation R-Square value was greater than or equal to the base R-Square value; then the test equation was used as, and replaced, the interaction model equation, and the test equation Root MSE and test equation R-Square values were used as the base Root MSE and base R-Square values, respectively.

7) Steps 4) through 6) were repeated until each of the 28 (F1-F14 and F1SQ-F14SQ) terms of the unadjusted interaction model equation were once removed.

Figure 2:
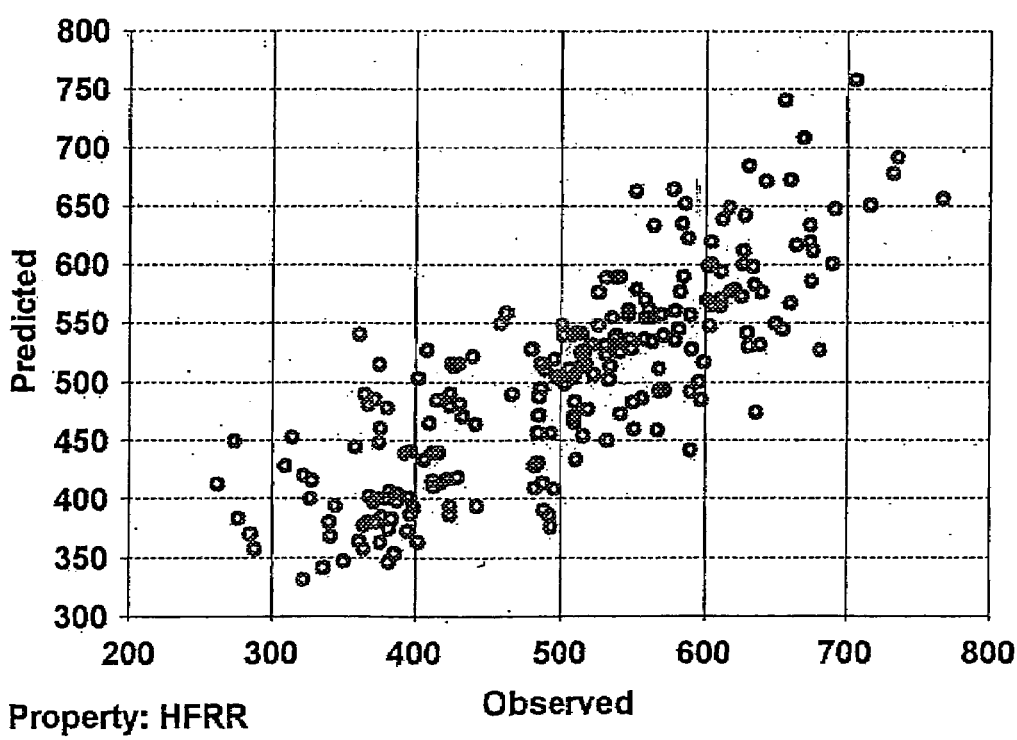
FIG. 2 depicts a plot of predicted vs. observed HFRR wear scar diameters based on the new interaction model equation.

The test equation Root MSE and test equation R-Square values for a test equation with the F5 term removed were 66.94 and 0.6655, respectively. Thus, because the test equation R-Square value is basically the same as the base R-Square value and the test equation Root MSE value is less than the base Root MSE value, this test equation was made the new interaction model equation and the test equation Root MSE and R-Square values replaced the base values. The plot of predicted vs. observed (measured) HFRR wear scar diameters for the 214 control diesel mixtures based on this equation is shown in FIG. 2.

Figure 3:
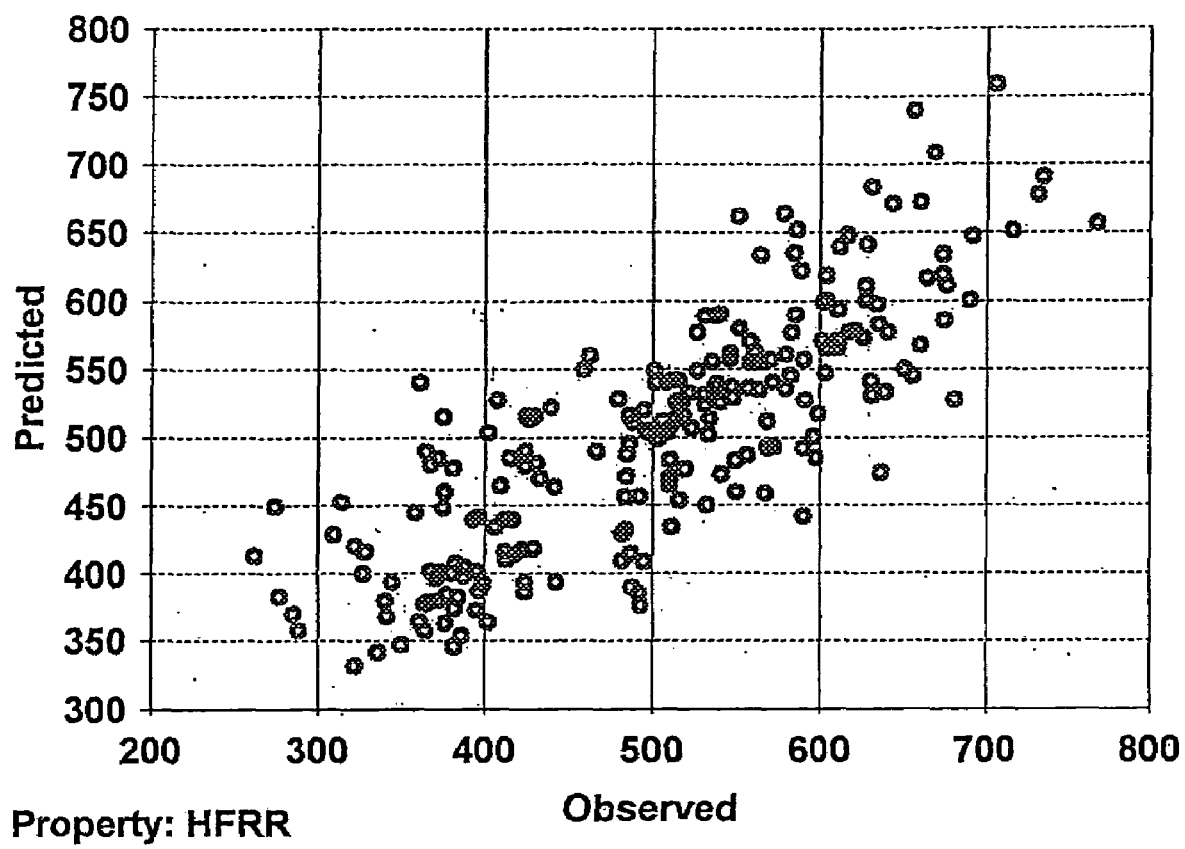
FIG. 3 depicts a plot of predicted vs. observed HFRR wear scar diameters based on the final interaction model equation.

The test equation Root MSE and test equation R-Square values for a test equation with the F5 and F13SQ terms removed were 66.77 and 0.6655, respectively. Thus, because the test equation R-Square value is the same as the base R-Square value and the test equation Root MSE value is less than the base Root MSE value, this test equation was made the new interaction model equation and the test equation Root MSE and R-Square values replaced the base values. The plot of predicted vs. observed (measured) HFRR wear scar diameters for the 214 control diesel mixtures based on the final interaction model equation is shown in FIG. 3.

The final interaction model equation version representing the HFRR wear scar diameter prediction equation for this Example is:

HFRR value=$Mo+M_1*F_1+M_2*F_2+\ldots+M_{14}*F_{14}+M_{15}*FSQ_1+M_{16}*FSQ_2+\ldots+M_{28}*FSQ_{14}$;
  wherein:

$M_0 = -9,427.1$
$M_1 = 61,650.3$
$M_2 = -26,419.2$
$M_3 = -14,772.9$
$M_4 = -3,044.2$
$M_5 = 0$
$M_6 = -10,716.7$
$M_7 = 8,289.0$
$M_8 = 800.4$
$M_9 = -5,258.7$
$M_{10} = 904.1$
$M_{11} = 4,494.4$
$M_{12} = -2,970.2$
$M_{13} = 528.5$
$M_{14} = 7,860.7$
$M_{15} = -40,319.7$

-continued $M_{16} = 19,397.4$
$M_{17} = 12,358.0$
$M_{18} = 1,652.7$
$M_{19} = 260.1$
$M_{20} = 7,184.1$
$M_{21} = -5,730.0$
$M_{22} = -329.4$
$M_{23} = 2,383.0$
$M_{24} = -277.6$
$M_{25} = -1,519.2$
$M_{26} = 961.4$
$M_{27} = 0$
$M_{28} = -6,587.9$ As can be seen from the Figures, the HFRR wear scar diameter prediction equation with the F5 and F13SQ terms removed is a good predictor of the measured HFRR wear scar diameter values.

Reasonable variations, modifications, and adaptations can be made within the scope of the disclosure and appended claims without departing from the scope of this invention.

That which is claimed is:

1. A method for predicting the High Frequency Reciprocating Rig (HFRR) wear scar diameter for a diesel product comprising the steps of:
   (a) selecting a control diesel product having various measured HFRR wear scar diameters as measured using the test method ASTM D-6079;
   (b) subjecting each of said control diesel products to mid-infrared (MIR) spectroscopy testing to thereby produce control property results for each of said control diesel products;
   (c) selecting an interaction model equation comprising a plurality of terms which relates MIR spectroscopy property results to HFRR wear scar diameters wherein said interaction model equation is based on multi-linear regression (MLR) analysis having the form $$P_x = M_0 + M_1 F_1 + M_2 F_2 + \ldots M_z F_z;$$

where
   $P_x$=value for property x; which corresponds to an HFRR wear scar diameter
   $F_z$=absorbance value from filter z; which correspond to said terms
   $M_z$=parameter estimate from filter z based on MLR analysis; which correspond to said coefficients for said terms
   $M_0$=intercept of model; and
   wherein the interaction model equation has 14 filters corresponding to the following functional groups:
   F1=methyl
   F2=methylene
   F3=Alkyl nitrate/Naphthalenes
   F4=Filter 3 baseline correction
   F5=Aromatic
   F6=Alkene
   F7=Alkene
   F8=Naphthalenes
   F9=Aromatic 3 adjacent hydrogens/Naphthalenes
   F10=Aromatic 4 adjacent hydrogens
   F11=Biphenyl
   F12=Aromatic symmetrical tri-substituted
   F13=Aromatic 5 adjacent hydrogens
   F14=Polynuclear Aromatics
   (d) establishing an HFRR wear scar diameter prediction equation by: (1) determining a set of coefficients for said terms of said interaction model equation by applying regression techniques to said control property results and said measured HFRR wear scar diameters, and (2) testing the statistical significance of each of said coefficients and said corresponding terms, and retaining from said interaction model equation only those of said coefficients and corresponding terms which are statistically significant, to thereby establish said HFRR wear scar diameter prediction equation;
   (e) subjecting said diesel product to MIR spectroscopy testing to thereby produce MIR spectroscopy property results; and
   (f) predicting the HFRR wear scar diameter value for said diesel product using said MIR spectroscopy property results in said HFRR wear scar diameter prediction equation.

2. A method as recited in claim 1 wherein step (d) (2) includes the following steps:
   (I) determining the base Root MSE value and the base R-Square value for said interaction model equation based on the regression in step (d) (1);
   (II) removing a term from said interaction model equation to form a test equation;
   (III) determining a test set of coefficients for said terms of said test equation by applying regression techniques to said control property results and said measured HFRR wear scar diameters;
   (IV) determining the test equation Root MSE value and the test equation R-Square value for said test equation based on the regression of Step (III);
   (V) if 1) said test equation Root MSE value is less than said base Root MSE value, and 2) said test equation R-Square value is greater than or equal to said base R-Square value; then: use said test equation as said interaction model equation, use said test equation Root MSE value as said base Root MSE value, and use said test equation R-Square value as said base R-Square value;
   (VI) repeating steps (II)-(V) until each of said plurality of terms of step (c) of claim 1 has been once removed from said interaction model equation in step (II); and
   (VII) using said interaction model equation resulting from step (VI) as said HFRR wear scar diameter prediction equation.

3. A method as recited in claim 1 wherein said diesel product comprises a diesel range material.

4. A method as recited in claim 1 wherein the number of said control diesel products selected in step (a) is at least about three times the number of said terms of said interaction model equation.

5. A method for producing a diesel product comprising the steps of:
   a) subjecting a sample of a diesel material to MIR spectroscopy testing to thereby produce MIR spectroscopy property results;
   b) predicting the HFRR wear scar diameter value for said diesel material using said MIR spectroscopy property results in said HFRR wear scar diameter prediction equation of claim 1;
   c) comparing said HFRR wear scar diameter value to a target HFRR wear scar diameter value;
   d) producing said diesel product by either:
      1) adding a lubricity additive to said diesel material if said HFRR wear scar diameter value is greater than said target HFRR wear scar diameter value to thereby produce said diesel product; or
      2) not adding a lubricity additive to said diesel material if said HFRR wear scar diameter value is less than said target HFRR wear scar diameter value, and utilizing said diesel material as said diesel product.

6. A method as recited in claim 5 wherein said method for producing said diesel product is performed at a refinery.

7. A method as recited in claim 5 wherein said method for producing said diesel product is performed at a product terminal.

8. A method as recited in claim 7 wherein steps a), b), and c) of claim 5 are performed at a laboratory or a retail site.

9. A method as recited in claim 5 wherein said target HFRR wear scar diameter value is the HFRR wear scar diameter specification value set out in the most current revision of ASTM D975.

10. A method as recited in claim 5 wherein said target HFRR wear scar diameter value is about 520 µm.

11. A method as recited in claim 5 wherein said target HFRR wear scar diameter value is about 480 µm.

12. A method as recited in claim 5 wherein each of said control hydrocarbon mixtures used in developing said HFRR wear scar diameter prediction equation of claim 1 comprise a diesel range material.

13. A method as recited in claim 5 wherein said interaction model equation used in developing said HFRR wear scar diameter prediction equation of claim 1 comprises at least 15 terms.

14. A method as recited in claim 5 wherein said interaction model equation used in developing said HFRR wear scar diameter prediction equation of claim 1 comprises at least 20 terms.

15. A method as recited in claim 5 wherein said interaction model equation used in developing said HFRR wear scar diameter prediction equation of claim 1 comprises at least 28 terms.

16. A method for predicting the HFRR wear scar diameter value for a diesel material comprising the steps of:
 a) subjecting a sample of a diesel material to MIR spectroscopy testing to thereby produce MIR spectroscopy property results;
 b) predicting the HFRR wear scar diameter value for said diesel material using said MIR spectroscopy property results and the HFRR wear scar diameter prediction equation of claim 1.

17. A method as recited in claim 16 wherein steps a) and b) are performed at a product terminal, a laboratory or a retail site.

18. A method as recited in claim 1, where said interaction model equation has the form:

$$P_x = M_0 + M_1 F_1 + M_2 F_2 + \ldots + M_{14} F_{14} + M_{15} FSQ_1 + M_{16} FSQ_2 + \ldots + M_{28} FSQ_{14},$$

where $SQ_1$-$SQ_{14}$ 0 are base R-Square values.

* * * * *